US008998818B2

(12) United States Patent
 Pranevicius et al.

(10) Patent No.: US 8,998,818 B2
(45) Date of Patent: Apr. 7, 2015

(54) NONINVASIVE METHOD TO MEASURE INTRACRANIAL AND EFFECTIVE CEREBRAL OUTFLOW PRESSURE

(76) Inventors: Henrikas Pranevicius, Kaunas (LT); Mindaugas Pranevicius, Forest Hills, NY (US); Osvaldas Pranevicius, New York, NY (US); David Liebeskind, Los Angeles, CA (US)

( * ) Notice: Subject to any disclaimer, the term of this patent is extended or adjusted under 35 U.S.C. 154(b) by 581 days.

(21) Appl. No.: 13/367,304

(22) Filed: Feb. 6, 2012

(65) Prior Publication Data
 US 2012/0136240 A1  May 31, 2012

Related U.S. Application Data

(63) Continuation-in-part of application No. 11/954,227, filed on Dec. 12, 2007, now Pat. No. 8,109,880.

(51) Int. Cl.
 | | |
 |---|---|
 | *A61B 5/05* | (2006.01) |
 | *A61B 5/00* | (2006.01) |
 | *A61B 5/03* | (2006.01) |
 | *A61B 5/021* | (2006.01) |
 | *A61B 5/0215* | (2006.01) |
 | *A61B 5/113* | (2006.01) |
 | *A61B 8/04* | (2006.01) |
 | *A61B 8/08* | (2006.01) |

(52) U.S. Cl.
 CPC .............. *A61B 5/031* (2013.01); *A61B 5/02108* (2013.01); *A61B 5/0215* (2013.01); *A61B 5/02152* (2013.01); *A61B 5/113* (2013.01); *A61B 8/04* (2013.01); *A61B 8/488* (2013.01); *A61B 2562/0219* (2013.01); *A61B 8/0808* (2013.01)

(58) Field of Classification Search
 USPC .......................... 600/309–344, 490–499, 561
 See application file for complete search history.

(56) References Cited

U.S. PATENT DOCUMENTS

2004/0087871 A1* 5/2004 Ragauskas .................... 600/561

OTHER PUBLICATIONS

Kampfl, et al. "Near Infrared Spectroscopy (NIRS) in Patients with Severe Brain Injury and Elevated Intracranial Pressure." Acta Neurochirurgica. 1997. 70:112-114.*
Alperin, at al.; Quantifying the Effect of Posture on Intracranial Physiology in Humans by MRI, etc.; Journal of Magnetic Resonance Imaging, vol. 22, pp. 591-596 (2005).

(Continued)

*Primary Examiner* — Patricia Mallari
*Assistant Examiner* — Tiffany Weston
(74) *Attorney, Agent, or Firm* — John F. Vodopia

(57) ABSTRACT

A system for detecting and measuring increased global or local intracranial pressure includes various devices for performing controlled occlusion of jugular cranial blood outflow and generating occlusion data related to said controlled occlusion, a cranial blood outflow pressure measurement device and a processor for processing jugular cranial blood outflow occlusion data and cranial blood outflow data to identify and/or measure a functional relationship between the jugular controlled occlusion and the jugular cranial blood outflow pressure. A device communicates the functional relationship a display device and/or a patient monitoring system. The processor also detects a state of equilibrium between the jugular cranial blood outflow pressure and the jugular occlusion pressure at occlusion. In yet another embodiment, intracranial and extracranial vessel compliance is measured by NIRS system, the equilibrated using external compression bladder, and equilibrium bladder pressure is displayed as local intracranial pressure.

7 Claims, 14 Drawing Sheets

(56) References Cited

OTHER PUBLICATIONS

Bratton, et al.; VIII. Intracranial Pressure. Thresholds; Journal of Neurotrauma, vol. 24, pp. S55-S58 (2007).

Bratton, et al.; VI. Indications for Intracranial Pressure Monitoring; Journal of Neurotrauma, vol. 24, pp. S37-S44 (2007).

Bratton, et al.; VII. Intracranial Pressure Monitoring Technology; Journal of Neurotrauma, vol. 24, pp. S45-S54 (2007).

Davie, et al.; Impact of Extracranial Contamination, etc.; American Society of Anesthesiologists, vol. 116, No. 4, pp. 834-840 (2012).

Dilenge, et al.; An Angiographic Study of the Meningorachidian Venous System; Radiology, vol. 108, pp. 333-337 (1973).

Gisolf, et al.; Human Cerebral Venous Outflow, etc.; The Physiological Society, pp. 317-327 (2004).

Edmonds, et al.; Near-Infrared Spectroscopy; Monitoring the Nervous System for Anesthesiologists and Other Health Care Professionals, (2012).

Orfanakis, et al.; Monitoring Intracranial Pressure; Monitoring the Nervous System for Anesthesiologists and Other Health Care Professionals, (2012).

Luce, et al.; A Startling Resistor Regulates Cerebral Venous Outflow in Dogs; The American Physiological Society, (1982).

Nlggeman, et al.; Positional Venous Mr Angiography: An Operator-Independent Tool to Evaluate, etc.; American Society of Neuroradiology, (2011).

Pearce; The Craniospinal Venous System; European Neurology, vol. 56, pp. 136-138 (2006).

Pellicer, et al.; Near Infrared Spectroscopy: A Methodology-Focused Review; Seminars in Fetal & Neonatal Medicine, vol. 16, pp. 42-49 (2011).

Pranevicus, et al.; Cerebral Venous Steal: Blood Flow Diversion With Increased Tissue, etc.; Neurosurgery, vol. 51, No. 5, pp. 1267-1274 (2002).

Tachtsidis, et al.; Investigation of Cerebral Haemodynamics by, etc.; Institute of Physics Publishing, vol. 25, pp. 437-445 (2004).

* cited by examiner

NONINVASIVE METHOD TO MEASURE INTRACRANIAL AND EFFECTIVE CEREBRAL OUTFLOW PRESSURE

CROSS-REFERENCE TO RELATED APPLICATIONS

This application is a continuation-in-part of patent application Ser. No. 11/954,227, filed on Dec. 12, 2007, and claims priority thereto in part under 35 U.S.C. §120 therefrom, all of the contents of which are incorporated by reference herein.

BACKGROUND OF THE INVENTION

The present invention relates broadly to the non-invasive measurement and monitoring of the absolute value of intracranial pressure.

Intracranial pressure (ICP) is closely related to cerebral blood flow (CBF). To a first approximation, CBF is determined by the cerebral perfusion pressure (CPP), due to their respective proportionality (CBF=CPP/Resistance). CPP is the difference between arterial blood pressure (BP) and intracranial pressure (ICP), that is, CPP=BP−ICP. Increase in ICP results in smaller values of CPP and CBF. Because of the difficulty of measuring CBF directly, BP and ICP are often measured to assess CPP. In a healthy individual, automatic regulation mechanisms in the body keep BP, ICP, and cerebral vascular resistance within a normal range and CBF is closely matched to the brain metabolic needs. These automatic regulation systems are often non-functional in brain trauma, stroke, hydrocephalic patients, and patients with liver or kidney failure, so that monitoring and management of ICP becomes a critical aspect of medical care. ICP>20 mmHg is recommended threshold for treatment in trauma patients (I Neurotrauma 2007; 24 Supp I: S55-8).

Current ICP monitoring techniques are generally grouped as either invasive or non-invasive.

Prior Art: Invasive ICP Measurement Methods

There are five common current invasive methods of measuring ICP which breach the skull: ventriculostomy, intraparenchymal catheter with built-in transducer (commonly fiberoptic), epidural transducer, subdural catheter, and subdural bolt. These have varying degrees of invasiveness. Of these methods, only a ventriculostomy can also be used to deliver therapy, which is usually draining fluid from the ventricles. The invasive methods, although medically accepted and routinely used, suffer from several drawbacks: (1) the transducer has to be calibrated before insertion; (2) the placement of the system requires a highly-trained individual; (3) there is a relatively short term (2-3 days) reliability and stability of the system, either because of leaks or plugging of the transducer, or inadvertently being disturbed, or being pulled out; (4) there are also associated risks of transducer placement such as brain damage and infection.

There are also additional drawbacks to current measurement techniques, for example:
a) many non-invasive techniques are not based on sound biophysical principles or do not take into account the interrelationship between biophysical principles;
b) many current techniques require expensive equipment and do not utilize existing equipment on hand;
c) many current techniques cannot be easily performed by personnel without special training;
d) most apparatus utilized for invasive techniques require accurate and of course regular calibration;
e) for the most part, invasive techniques allow measurements only in the limited setting of an intensive care unit, e.g., not in ambulatory, in field, in non-acute care community nor private in-home settings;
f) some current techniques do not always provide for reproducible measurements for the monitoring purposes;
g) known non-invasive techniques require head or orbital contact, ruling out use in patients with external head and/or orbital injuries -the specific patient population who likely need this measurement most; and
h) many known non-invasive techniques use ultrasound and as such expose brain to the high intensity acoustic energy.

Due to the many problems associated with invasive techniques for measuring ICP, standard medical protocol is to monitor ICP only for patients with scores of 8 or less on the Glasgow; Neurotrauma, Coma Scale Guidelines for the Management of Severe Traumatic Brain Injury (24 Supp.; 3rd edition 2007).

It would be desirable, therefore, to realize non-invasive techniques and apparatus for detecting and measuring increased global or local intracranial pressure (ICP) which overcome the shortcomings of the prior art, to facilitate monitoring ICP of patients with Glasgow scores higher than 8 and monitoring ICP in healthy individuals under severe environmental stress, such as astronauts, divers, and submariners, without limitation.

SUMMARY OF THE INVENTION

The present invention presents a method for readily and accurately detecting and measuring increased global or local intracranial pressure (ICP) noninvasively and a system for implementing same The inventive system and method for detecting and measuring increased global or local intracranial pressure (ICP) noninvasively also determines whether cerebral perfusion pressure (CPP) depends on intracranial pressure (ICP) or central venous pressure (CVP). As used herein, central venous pressure (CVP) is equivalent to the mean pressure of the blood leaving the cranium through the interconnected craniospinal venous system (i.e., the jugular vein and the vertebral venous plexus) emptying into the vena cava.

The inventive method is based in sound biophysical principles, is easily performed by personnel without special training, requires little or no calibration, allow measurements outside the ICU, for example, ambulatory, field and home settings, provides reproducible measurements for the monitoring purposes, operates independently of the presence of external head and/or orbital injuries, and minimizes brain exposure to high intensity acoustic energy. For that matter, the inventive system for measuring intracranial pressure noninvasively and determining whether CPP depends on ICP or CVP is relatively inexpensive.

In an embodiment, the method includes registering cerebral hemodynamics, then changing pressure in the jugular veins to affect cerebral venous outflow, estimating the pressure in jugular veins and establishing jugular pressure value when an abrupt change in the cerebral hemodynamic occurs. The abrupt change in the cerebral hemodynamics reflects occurrence of a jugular venous (JV) outflow redistribution to vertebral venous plexus (VVP). A jugular vein pressure value at that point (redistribution to the VVP) is displayed as an absolute value of intracranial pressure.

In another embodiment transmural pressure of the intracranial and extracranial vessels is equilibrated using inflatable bladder to compress extracranial vessels: compliance and pulsatility of extracranial and intracranial vessels becomes the same at the point of equilibrium, and bladder pressure is displayed as the intracranial pressure. This method allows detection not only global intracranial pressure, but also detection of regional intracranial pressure differences.

In another embodiment, the invention provides a system for detecting and measuring increased global or local intracranial pressure. The system comprises means for performing controlled occlusion of jugular cranial blood outflow and generating occlusion data related to said controlled occlusion, a cranial blood outflow pressure measurement device and a processor for processing jugular cranial blood outflow occlusion data and cranial blood outflow data to identify and/or measure a functional relationship between the jugular controlled occlusion and the jugular cranial blood outflow pressure.

The system may also include a device for communicating the functional relationship a display device and/or a patient monitoring system. The processor also detects a state of equilibrium between the jugular cranial blood outflow pressure and the jugular occlusion pressure at occlusion. The measured jugular occlusion pressure associated with the state of equilibrium is proportional or substantially equivalent to the intracranial pressure. The means for performing controlled occlusion are any of the group consisting of a hydrostatic occlusion device, an external cuff occlusion device, intraluminal occlusion device comprising with the balloon, a tilt table and a tonometer.

In another embodiment, the system comprises one or more near infrared spectroscopy (NIRS) sensors positioned at the subject cranium for identifying changes in outgoing blood flow as a function of detected pulsed excitations. Pulsed excitations follow either the cardiac cycle or the breathing cycle. The pulsed excitations are generated by a cuff and cuff controller of by an oscillatory device positioned proximate a jugular vein. Controlled occlusion is achieved by creating hydrostatic gradient between the point of cranial blood outflow and the right atrium of the subject's heart though tilting to decrease a difference between the internal intravascular pressure and external atmospheric pressures.

The cranial blood outflow pressure measurement device is any device of the group consisting of an ultrasound sensor device operating based on detected Doppler shift, or duplex scan, by a device that identified thermodilution, by an angiography device, by a magnetic resonance angiography device and by an occlusion plethysmography device. The cranial blood outflow pressure measurement device measures jugular outflow volume using one of the group consisting of rheography, impedance plethysmography, photoplethysmography, strain-gage plethysmography). The cranial blood outflow pressure measurement device measures arterial (or venous) pulse transmission to the NIRS sensor to measure pulsatility index. Preferably, the near infrared transmission or absorption characteristics of the cranium provides a basis for obtain the external compression pressure when same becomes equal to the intracranial pressure and external oscillation begins to transmit to the cranium.

The critical point is the transition between gradual increase of the said parameter and a plateau or asymptomatic peak in pressure at which cranial blood outflow pathway pressure causes the blood outflow to be diverted to the alternative outflow pathway such as the vertebral venous plexus (VVP). Preferably, the critical point is the transition between the plateau and a gradual increase of the parameter where intracranial pressure (ICP) becomes equal to the occluded pathway's pressure and the outflow does not divert to the VVP and. ICP is directly affected by cranial blood outflow pressure.

In another embodiment, the invention provides a method for detecting and measuring increased global or local intracranial pressure. The method includes performing controlled occlusion of jugular cranial blood outflow, generating occlusion data related to said controlled occlusion, processing jugular cranial blood outflow occlusion data and blood outflow data relating to the controlled occlusion to identify and/or measure a functional relationship between the jugular controlled occlusion and the jugular cranial blood outflow. The processing includes detecting a state of equilibrium between the jugular cranial blood outflow pressure and the jugular occlusion pressure. The measured jugular occlusion pressure associated with the state of equilibrium is proportional or substantially equivalent to the intracranial pressure.

Preferably, performing the controlled occlusion includes creating a hydrostatic gradient between the point of cranial blood outflow and the right atrium of the subject's heart though tilting to decrease a difference between the internal intravascular pressure and external atmospheric pressures and most preferably performing the controlled occlusion includes exerting external pressure to implemented a controlled constriction of blood flow exiting the cranium through the jugular veins. The step of generating occlusion data includes measuring cranial blood volume and/or measuring near infrared transmission or absorption characteristics. ICP is detected by identifying a pressure at which cranial blood outflow pathway pressure causes the blood outflow to be diverted to the alternative outflow pathway such as the vertebral venous plexus (VVP).

In another embodiment, the invention provides a method for detecting and measuring increased global or local intracranial pressure within a subject cranium that includes using non-invasive infrared spectroscopy measuring means, creating and investigating a first light pathway through a portion of extracranial tissue, including blood pathways, surrounding the subject cranium and a second light pathway through a portion of intracranial tissue, including blood pathways, within the subject cranium, wherein the portion of extracranial tissue is proximate the portion of intracranial tissue and applying a pressure at a measurable external pressure value to compel the non-invasive infrared spectroscopy measuring means against the subject cranium while detecting a first signal corresponding to a constant or average blood pressure (DC), and a second signal corresponding to a peak, pulsed blood pressure (AC) in both the extracranial and intracranial portions.

The measured external pressure value, the signals in the extracranial portion and the intracranial portion are processed until a state of compliance or equilibrium between the extracranial and intracranial blood vessels is detected, the measured pressure at which state corresponding to the subject cranium's intracranial pressure (ICP) proximate the non-invasive infrared spectroscopy measuring means. The processing includes processing both the first and second signals in the extracranial portion and the intracranial portion. In the step of applying, the first and second signals detect either blood flow or blood volume in the respective extracranial and intracranial regions.

The non-invasive spectroscopy means comprises at least one NIRS sensor in electronic communication with an NIRS spectroscopy device and attached to the subject cranium capable of generating and investigating light path through both the extracranial portion and the intracranial portion. The pulsatile nature reflected in the pulsed blood pressure (AC) is driven by the subject's heart or breathing. Alternatively, the pulsatile nature reflected in the pulsed blood pressure (AC) is driven by oscillatory device. Preferably, the oscillatory device is positioned at or near the subject's neck to affect the arterial blood vessels delivering blood to the extracranial and the intracranial blood pathways.

BRIEF DESCRIPTION OF THE DRAWING FIGURES

The present invention can best be understood in connection with the accompanying drawings. It is noted that the invention is not limited to the precise embodiments shown in drawings, in which.

Figure 5A:
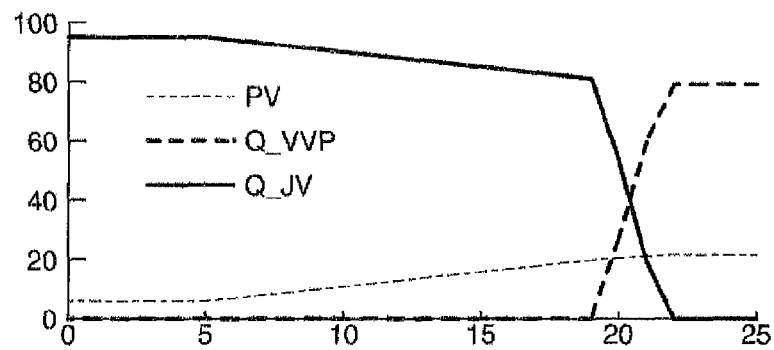
Figure 5B:
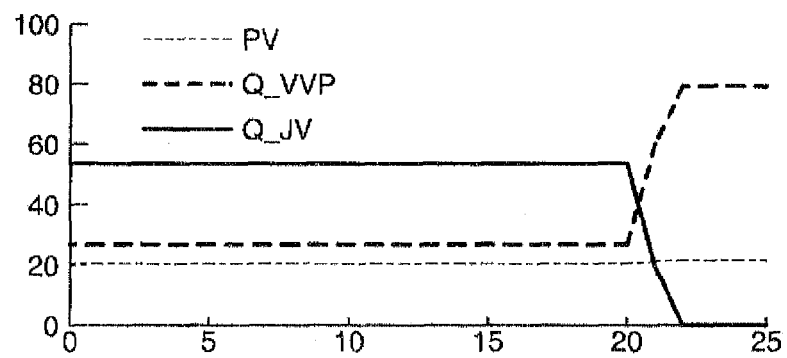
Figure 5C:
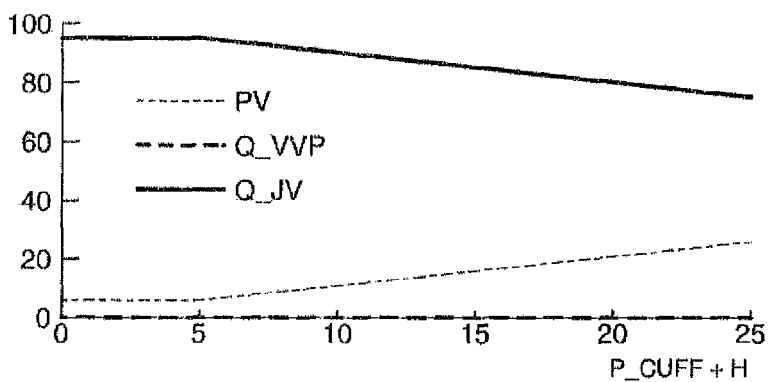
Figure 6:
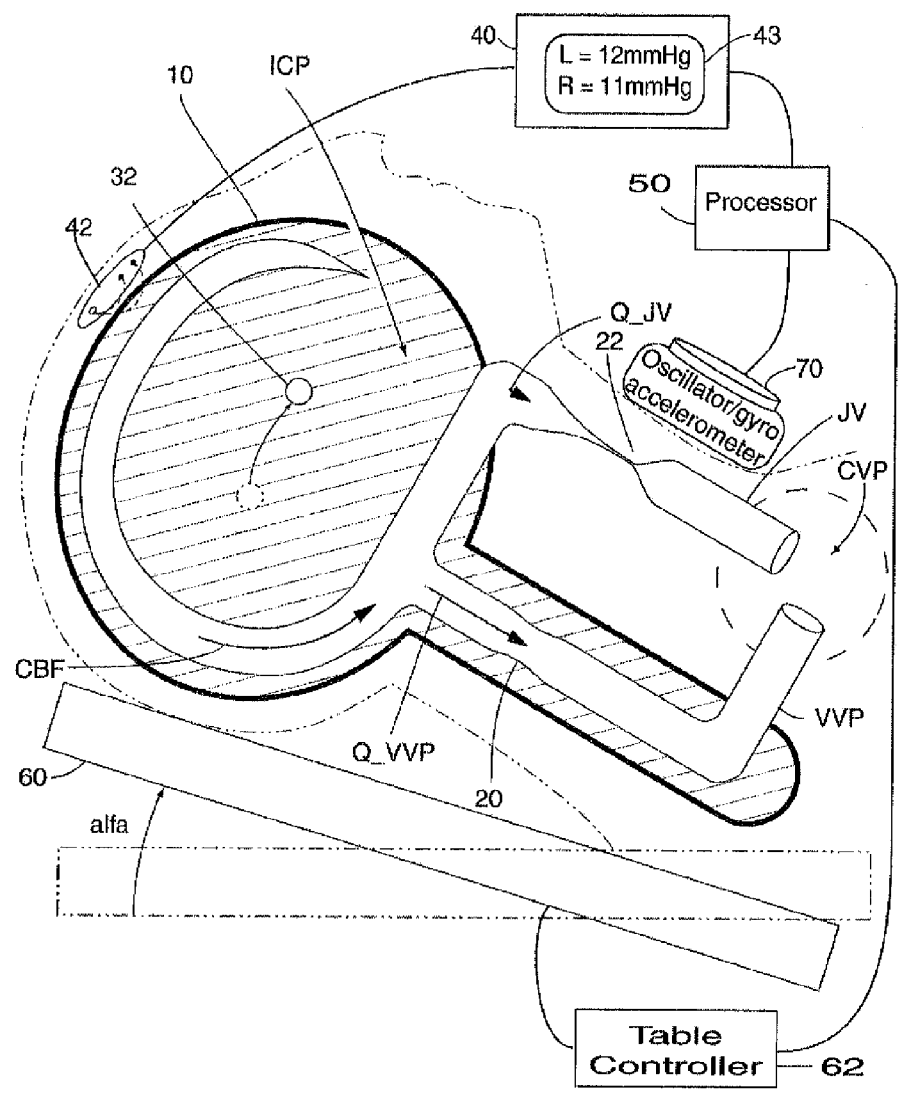
Figure 7:
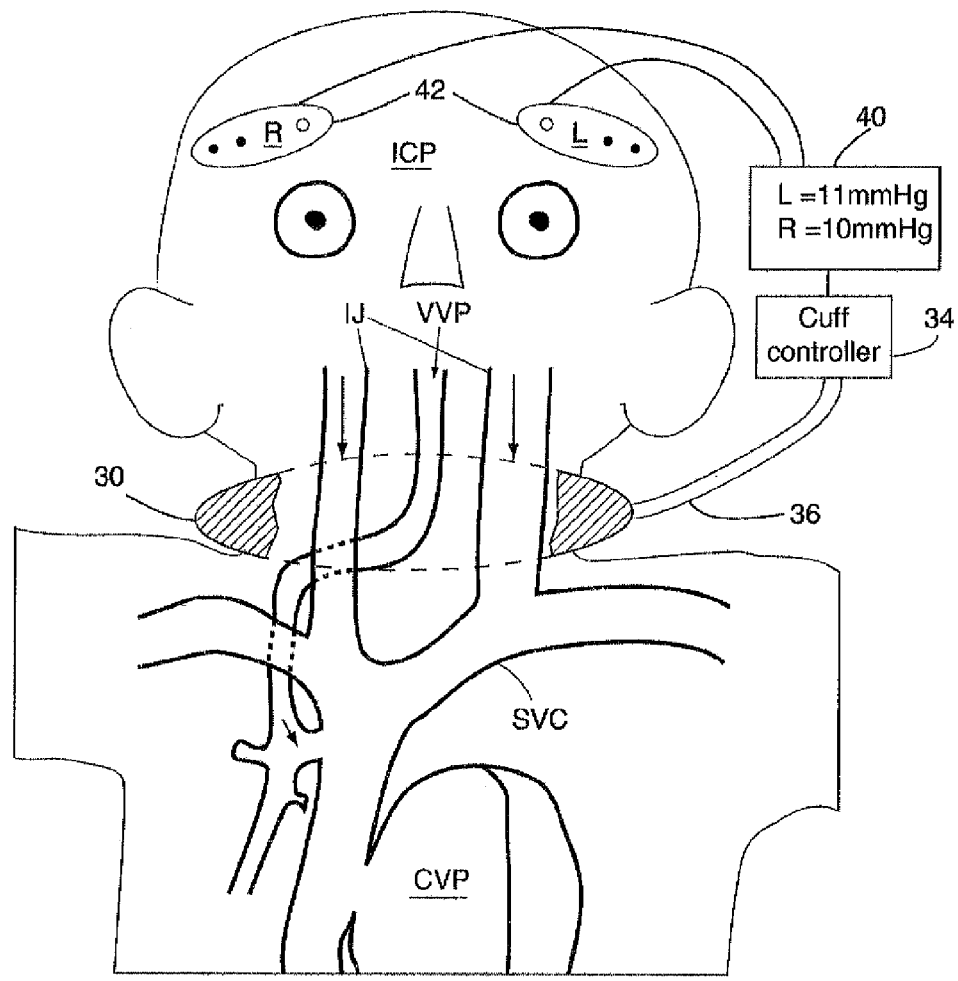
Figure 8:
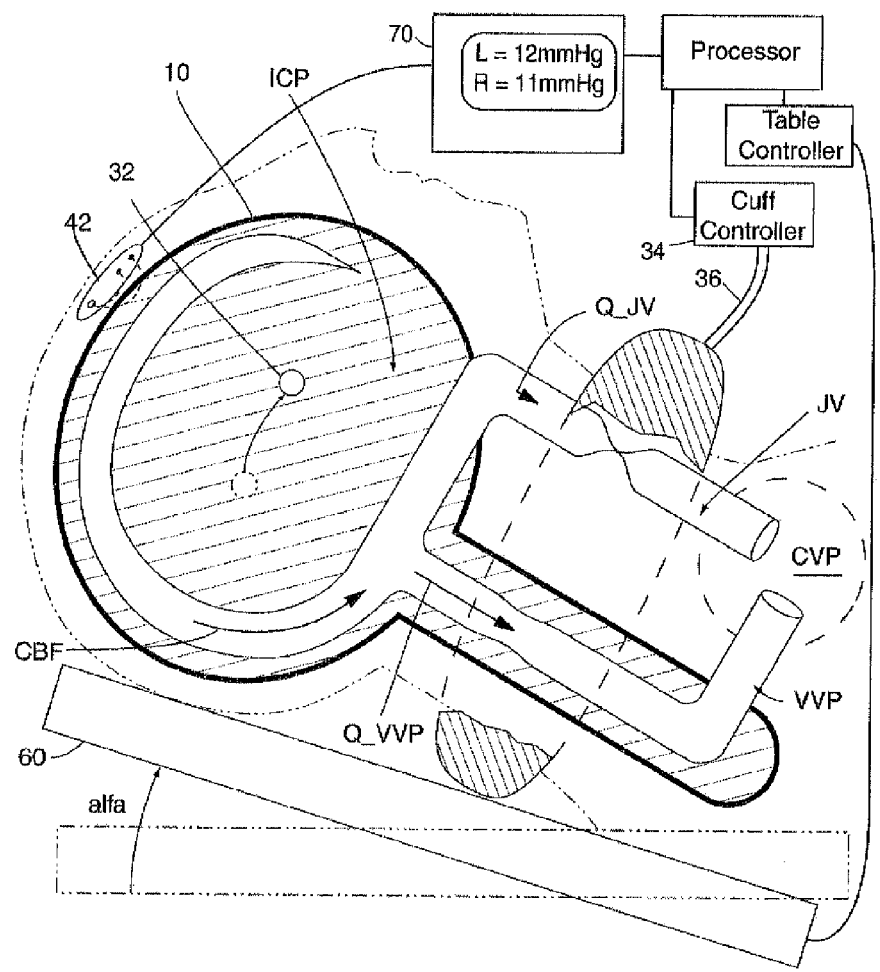
Figure 9:
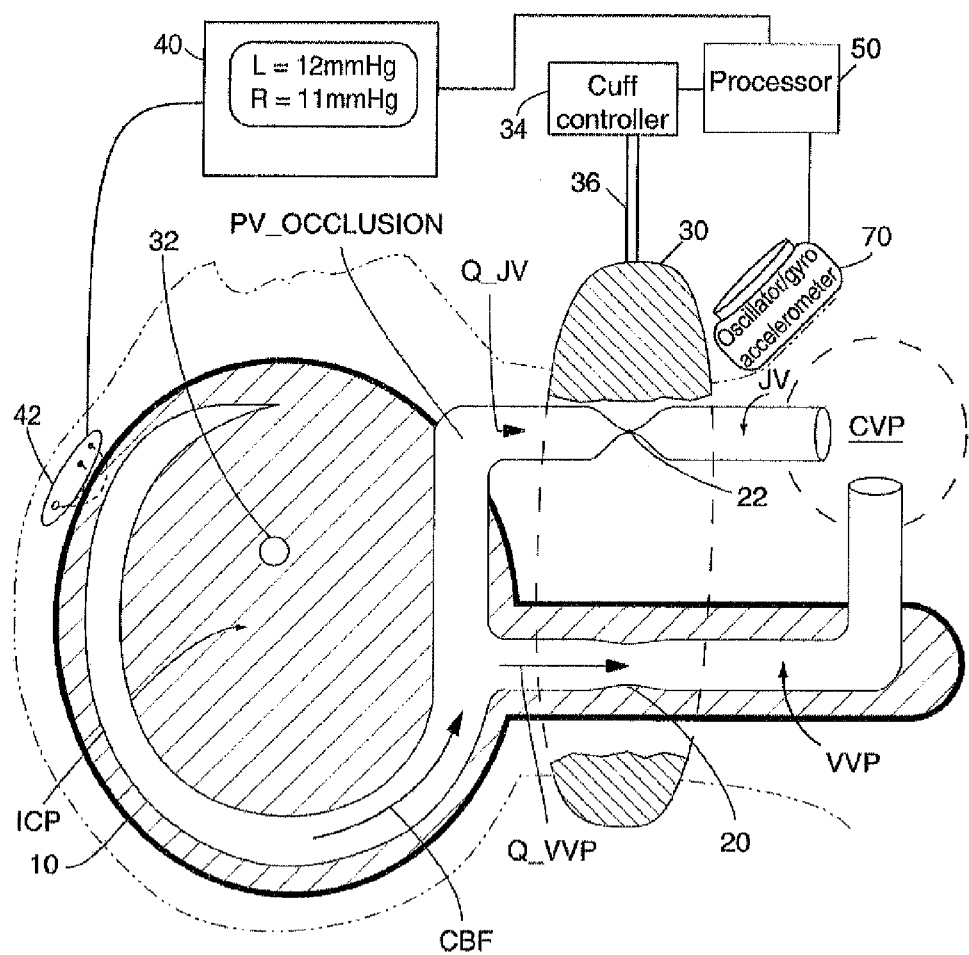
Figure 10:
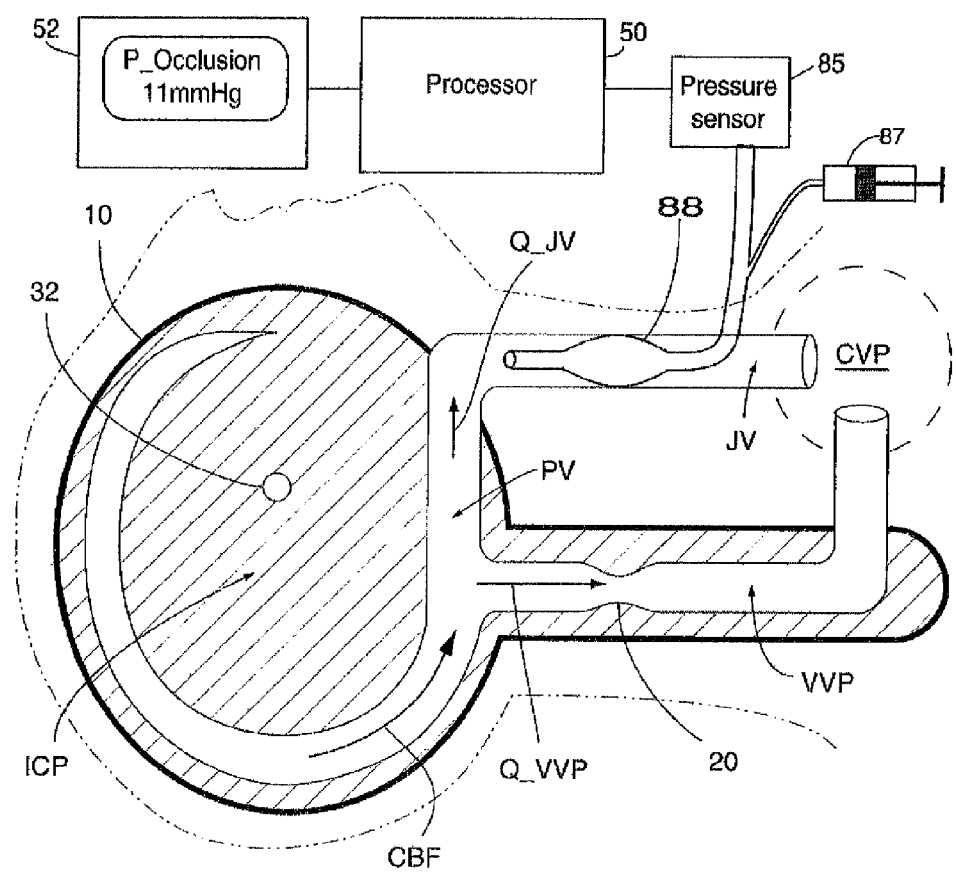
Figure 11:
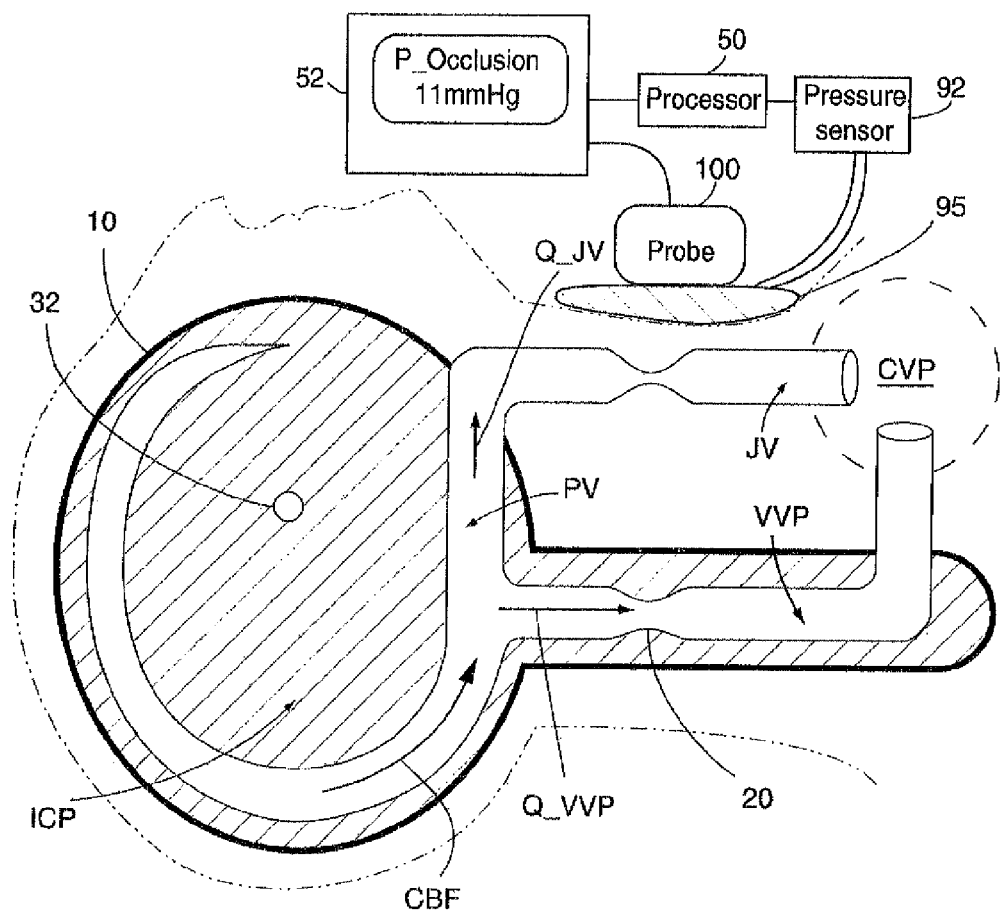
Figure 12:
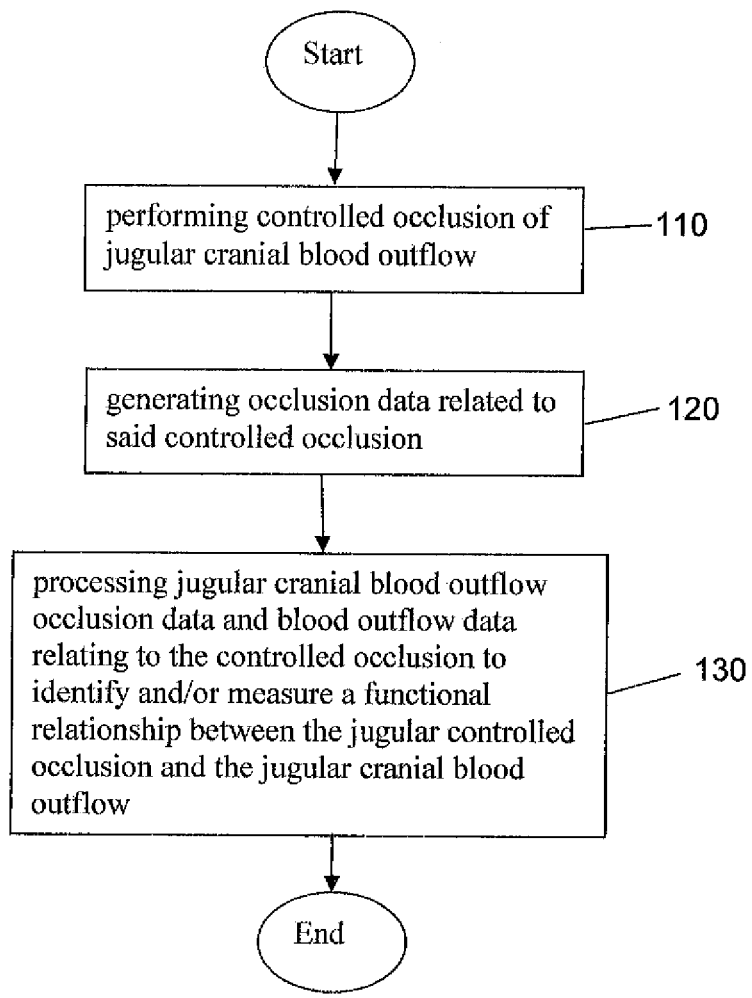
Figure 13:
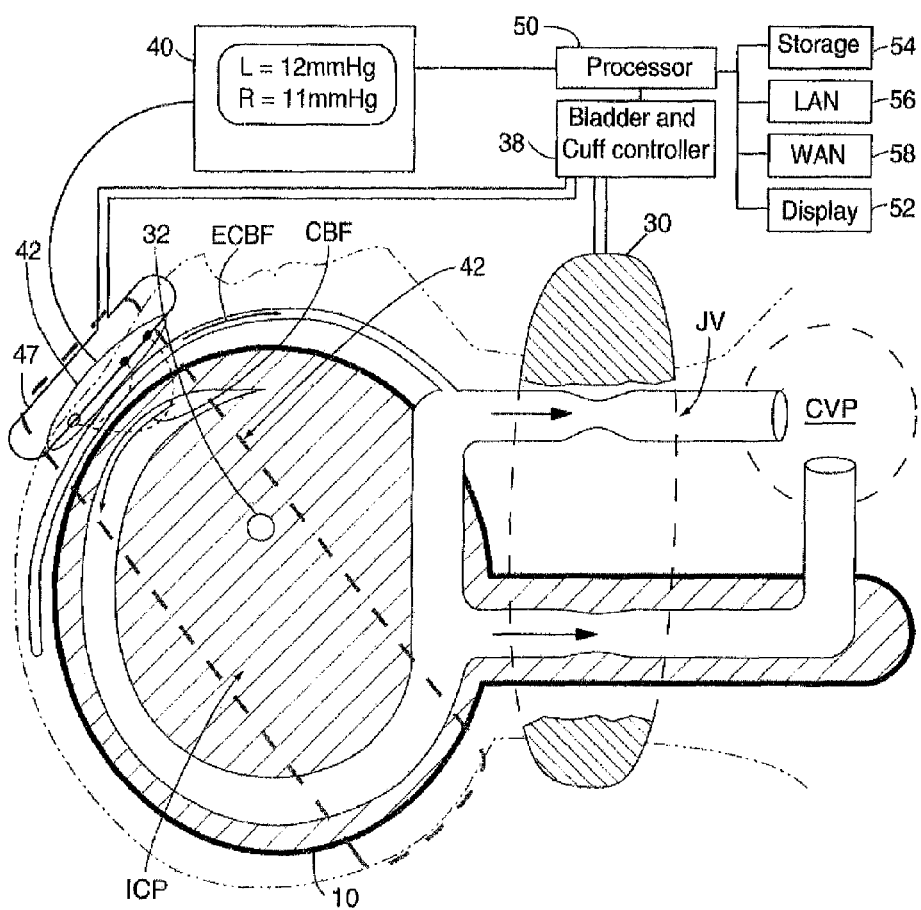
Figure 14:
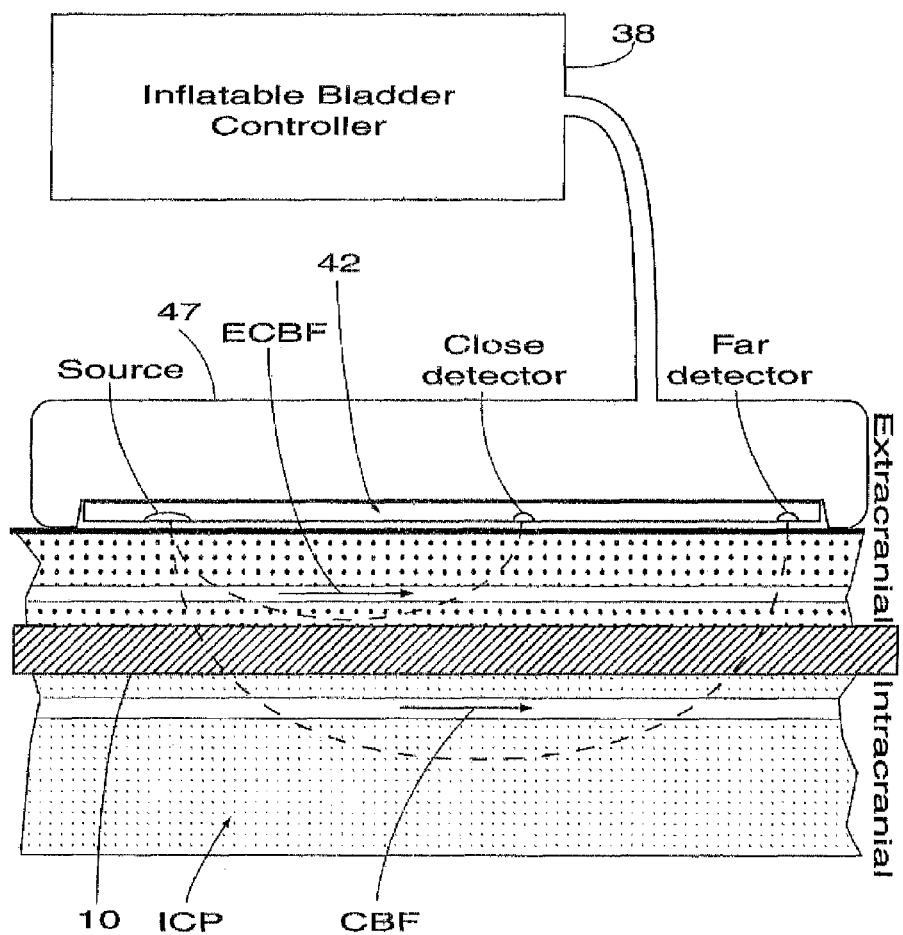

FIGS. 5A-5C (CVP=5, ICP=20), 5B (CVP=20, ICP=20) and 5C (CVP=5, ICP=30) are simulated plots of venous blood pressure (PV), jugular venous outflow (Q_JV), vertebral venous plexus outflow (Q_VVP) as a function of pressure in mm Hg flow, where P_CUFF_MAX=25;

FIG. 6 is a schematic diagram depicting outflow diversion from jugular veins (JV) to vertebral venous plexus (VVP) with head elevation controlled by use of a calibrated tilt table, and measurement/verification by use of induced oscillation detected by a near infrared sensor (NIRS);

FIG. 7 is a schematic diagram depicting outflow diversion from jugular veins (JV) to the vertebral venous plexus (VVP) with cervical cuff compression and measurement/verification by use of induced oscillation detected by a near infrared sensor (NIRS) to localize ICP in the right and left hemispheres;

FIG. 8 is a schematic diagram depicting outflow diversion from jugular veins (JV) to vertebral venous plexus (VVP) with head elevation controlled by use of a calibrated tilt table in combination with cuff occlusion, and measurement/verification by use of induced oscillation detected by a near infrared sensor (NIRS);

FIG. 9 is a schematic diagram depicting outflow diversion from jugular veins (JV) to the vertebral venous plexus (VVP) with cervical cuff compression occluding JV venous outflow such that induced oscillation by centrally located oscillator are no longer detected by a near infrared sensor (NIRS);

FIG. 10 is a schematic diagram depicting outflow diversion from jugular veins (JV) to the vertebral venous plexus (VVP) using an occlusion balloon inserted in one or both jugular veins to measure occlusion pressure directly;

FIG. 11 is a schematic diagram depicting a liquid occlusion cuff to provide occlusion pressure measured by a controller as well as window for observation of the jugular collapse using an ultrasound probe;

FIG. 12 is a schematic flow diagram depicting program flow in another embodiment of the inventive method;

FIG. 13 is a schematic diagram depicting outflow diversion from jugular veins (JV) to the vertebral venous plexus (VVP) with cervical cuff compression, and measurement/verification by use of induced oscillation (at $P_{cuff}=P_{occlusion}$) detected by a near infrared sensor (NIRS) operation of which is complemented by a compressive cranial cuff device 47; and FIG. 14 presents is a more detailed view of the compressive cranial cuff 47 and one of the NIRS sensors 42, as shown in FIG. 13.

DETAILED DESCRIPTION OF THE INVENTION

The following is a detailed description of example embodiments of the invention depicted in the accompanying drawings. The example embodiments are in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

The invention provides method and apparatus for detecting and measuring increased global or local intracranial pressure (ICP) (both invasively and non-invasively) as well as whether ICP or CVP determines effective cerebral outflow pressure. The theoretical basis of the invention has a theoretical basis in an intracranial model based on the Starling resistor; Luce, J M, Huseby, J S, Kirk W, Butler, J., Starling Resistor Regulates Cerebral Venous Outflow In Dogs, App. Physiol. (53(6), 1496-1503, December 1982) and on a theory of cerebral blood flow diversion ("cerebral venous steal model'), which demonstrated outflow redistribution between the pathways with different extrinsic pressure; Pranevicius, M, Pranevicius, O, Cerebral Venous Steal: Blood Flow Diversion with Increased Tissue Pressure, Neurosurgery (November; 51(5): 1267-73; discussion 1273-4, 2002).

Starling resistor effect is found to exist in the intracranial veins (JV and VVP), that is, pressure in the collapsible intracranial veins is found to be substantially equal to intracranial pressure (ICP); Luce, J M, Huseby, J S, Kirk W, Butler, J., Starling Resistor Regulates Cerebral Venous Outflow In Dogs; App. Physiol. (53(6):1496-1503; 1982 December). Collapsible intracranial veins and veins of vertebral venous plexus VVP are exposed to ICP and may be modelled (i.e., reflect behavior) of Starling resistors. The Starling resistor model is used to describe behavior and flow within collapsible veins, whether within the vertebral venous plexus (VVP) or jugular veins (JV), as a function of extrinsic compression; Pranevicius, M, Pranevicius, O., Cerebral Venous Steal: Blood Flow Diversion with Increased Tissue Pressure; Neurosurgery (51(5):1267-73; November 2002). That is, internal jugular veins act as Starling resistors, a collapse of which 22 is occurs whenever venous pressure becomes negative in regard to atmospheric pressure with head-up tilt. J, van Lieshout J J, van Heusden K, Pott F, Stok W J, Karemaker J M. Human cerebral venous outflow pathway depends on posture and central venous pressure. J Physiol. 2004 Oct. 1; 560 (Pt 1):317-27.

Figure 1:
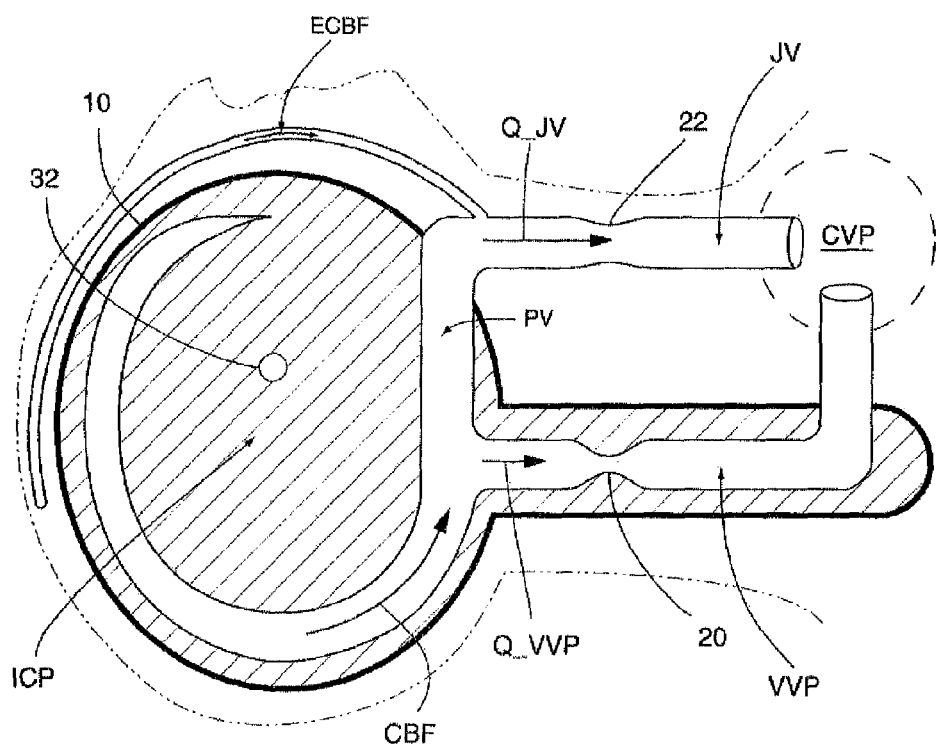
FIG. 1 is a schematic diagram depicting cerebral blood outflow pathways, presented to highlight the principles of the inventive system and method.

FIG. 1 depicts cerebral blood outflow pathways in a patient's cranium 10, including the external acoustic meatus 32. Blood leaves the cranium 10 through the interconnected. craniospinal venous system (JV and VVP) with mean outflow blood pressure PV. These outflow pathways have multiple anastomoses and form craniospinal venous system; Pearce, J M., The Craniospinal Venous System, Eur. Neural. (56(2) i 36-8; 2006). Please note that the extracranial cerebral blood flow (ECBF), upon leaving the extracranial tissue, empties into the JV. A collapsible segment of the intracranial and intraspinal veins (20) and a collapsible segment of the jugular veins 22 (as shown) are operated upon by intracranial pressure (ICP). Both sets of veins empty into the vena cava, which displays a central venous pressure CVP. When extrinsic pressure is smaller than inflow pressure but higher than the outflow pressure, flow is determined by difference between inflow and extrinsic pressure, while outflow pressure does not affect the flow. When extrinsic pressure is smaller than the outflow pressure, it has no effect on flow. Outflow is then determined by the difference between inflow and outflow pressure.

As used herein, venous drainage via the spinal canal is depicted by Q_VVP and extraspinal drainage is depicted as jugular outflow (Q_JV). In this functional definition, Q_JV comprises flow via jugular veins, deep cervical veins and the extraspinal venous plexus. The functional difference between jugular and intraspinal pathways is that extrinsic neck pressure obstructs jugular but not the vertebral outflow. Proximal venous pressure (PV) is understood to approximate ICP or central venous pressure (CVP), whichever is higher (CVP<=PV>=JCP). Total venous outflow CBF is distributed between jugular veins JV (Q_JV) and VVP (Q_VVP); CBF=Q_JV+Q_VVP.

Figure 2A:
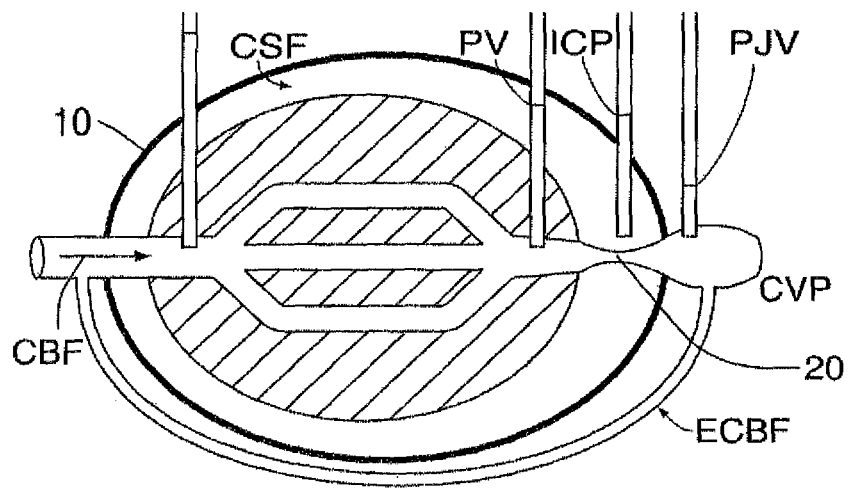
FIG. 2A is a diagram depicting cerebral blood flow outflow pathways highlighting an intracranial pressure and venous pressure relationship corresponding to a Starling resistor model.

Prior Art FIG. 2A depicts a model representative of cerebral blood outflow pathways and the effect/relationship between intracranial pressure and venous pressure in accordance with a Starling resistor model, Arterial extracranial cerebral blood (ECBF) and arterial intracranial blood flow are shown (to the left in FIG. 2A) entering the external head tissue and the inner cranium, respectively. Total cranial (arterial) inflow pressure is represented by the column of Hg (to the left in the figure) prior to a split (representing capillary structure) through multiple pathways. At a far side of, or downstream of the split, a collapsible intraspinal vein 20 and columns of Hg just prior to and just past (in a flow direction toward the vena cava) the collapsible intraspinal vein 20. The column of HG just prior to collapsible intraspinal vein 20 represents the intracranial outflow pressure (PV), where the column of HG just after the collapsible intraspinal vein 20 represents the extracranial JV pressure (PJV), at or near the juncture with the ECBF. The column of HG identified as ICP represents the intracranial pressure (ICP) of the cerebral spinal fluid (CSF).

Figure 2B:
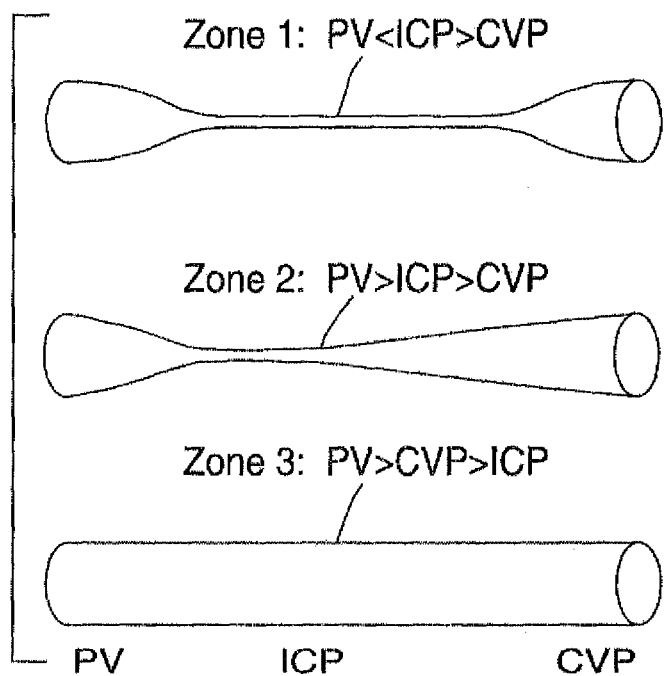
FIG. 2B depicts levels of interrelationships between intracranial pressure (ICP), venous blood pressure (PV), jugular venous blood pressure (PJV), central venous pressure (CVP) and occlusion.

Prior art FIG. 2B depicts three zones reflective of an amount of occlusion found in the intraspinal vein 20 as a function of ICP, relative ICP. In Zone 1 (PV<ICP>CVP), ICP is shown to be greater than bath PV and CVP resulting in a substantially occluded intraspinal vein 20. In Zone 2 (PV>ICP>CVP), ICP is indicated to be less than PV but greater than CVP, resulting in a partial occlusion of intraspinal vein 20. In Zone 3 (PV>CVP>ICP), proximal venous pressure (PV) is greater that central venous pressure (CVP), where CVP is still larger that ICP, resulting in substantially occlusion free outflow through intraspinal vein 20 (as shown). Please note that PJV is close to CVP, but there is small, usually negligible gradient between PJV and CVP. PV is cerebral venous pressure, which approximates ICP if ICP>PJV.

Figure 3:
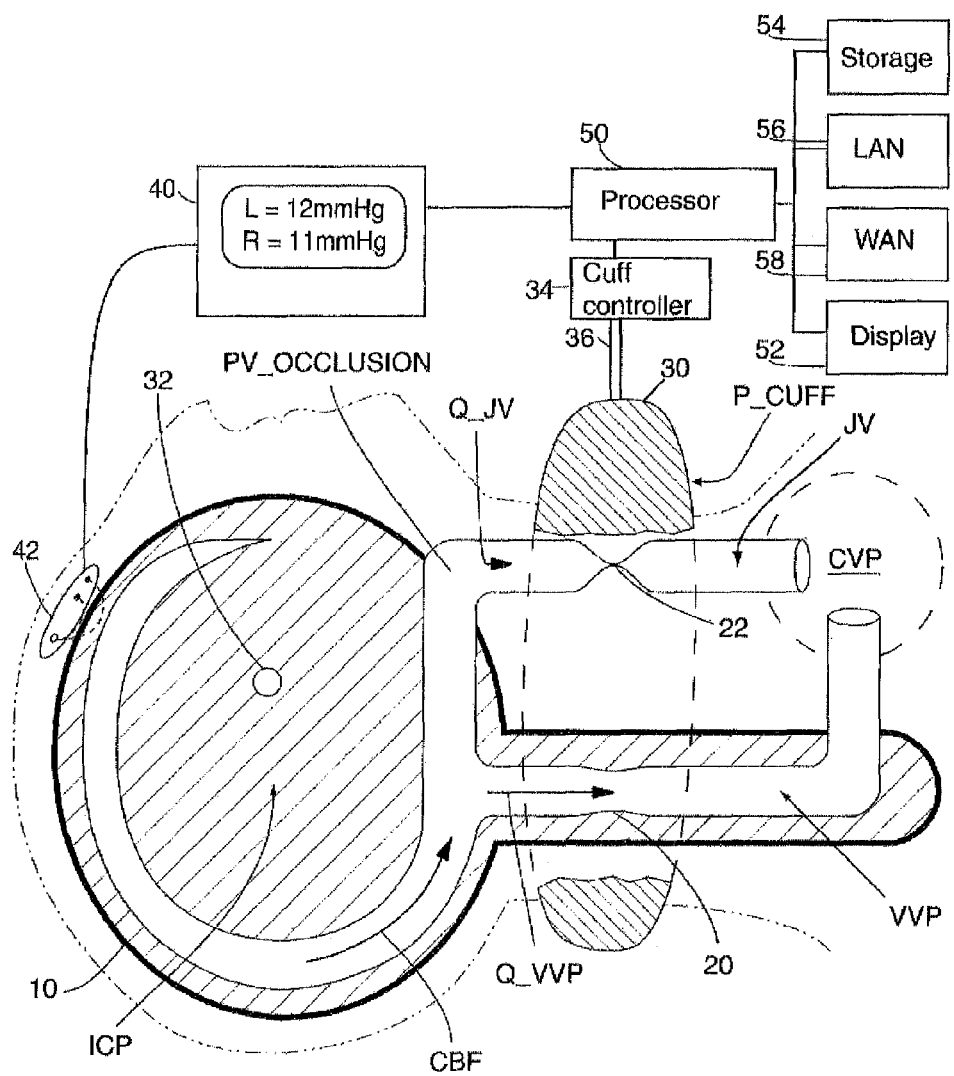
FIG. 3 is a schematic diagram depicting outflow diversion from jugular veins (JV) to the vertebral venous plexus (VVP) with cervical cuff compression, and measurement/verification by use of induced oscillation (at $P_{cuff}=P_{occlusion}$) detected by a near infrared sensor (NIRS)

FIG. 3 depicts one embodiment of a system for detecting and measuring increased global or local intracranial pressure of the invention. Like in FIG. 1, cerebral blood outflow (CBF) is depicted as leaving the cranium 10 through the interconnected craniospinal venous system (JV and VVP) with mean outflow blood pressure PV, wherein a collapsible segment of the intracranial and intraspinal veins (20) and a collapsible segment of the jugular veins 22 are assumed to be operated upon by intracranial pressure (ICP) before emptying into the vena cava at CVP. In the supine position, a substantial part of the venous outflow (CBF at PV) from the cranium flows through via jugular veins JV (i.e., Q_JV >Q_VVP (FIG. 1). During head up tilt, blood outflow redistributes to the VVP and the jugular veins JV partially collapse (Gisolf, J, van Lieshout, J J, van Heusden, K, Pott, F, Stok, W J, Karemaker, J M. (2004) Human cerebral venous outflow pathway depends on posture and central venous pressure. J Physiol 560: 317-27), which tilt-induced jugular vein collapse is described in more detail in cooperation with FIG. 6, below.

In the FIG. 3 system, blood outflow redistribution is induced (from JV to VVP) with a cervical cuff 30. A cuff controller 34 controls and amount of fluid compelled into the cervical cuff 30, which in turn exerts extrinsic pressure P_Cuff on the jugular veins. Extrinsic pressure P_Cuff constricts the jugular veins (JV) and blood flow therethrough, affecting jugular venous outflow pressure. Depending on a patient's ICP, increasing P_Cuff causes the jugular veins to collapse 22 (see FIGS. 2 and 5), where CBF is redistributed from JV to VVP. A cerebral near infrared spectroscopy (NIRS) device 40 connected to and operating with (one or more) near infrared spectroscopy (NIRS) sensor(s) 42 in included in the system to verify when occlusion at 22 occurs, as change in P_Cuff is monitored (see display section 43). Operation of NIRS sensors 42 is explained in greater detail with the descriptions of FIGS. 13 and 14, below.

A processor 50 is programmed to control operation of both the cerebral/somatic oximeter 40 and the cuff controller 34 (and therefore P_Cuff). Near infrared oximetry sensor (NIRS) 42 measures blood volume, haemoglobin volume and oxygenated/deoxygenated haemoglobin ratios, based on multiple wavelength absorption or phase shift. Processor 50 also is shown connected to a display device 52, a digital storage device 54, a local area network (LAN) 56 (for example, a local hospital network) and a wide area network (WAN) 58. WAN 58 may comprise a series of networks interconnected via the Internet (not shown). All pertinent data may be displayed on display device 52 in any known data form.

Figure 4:
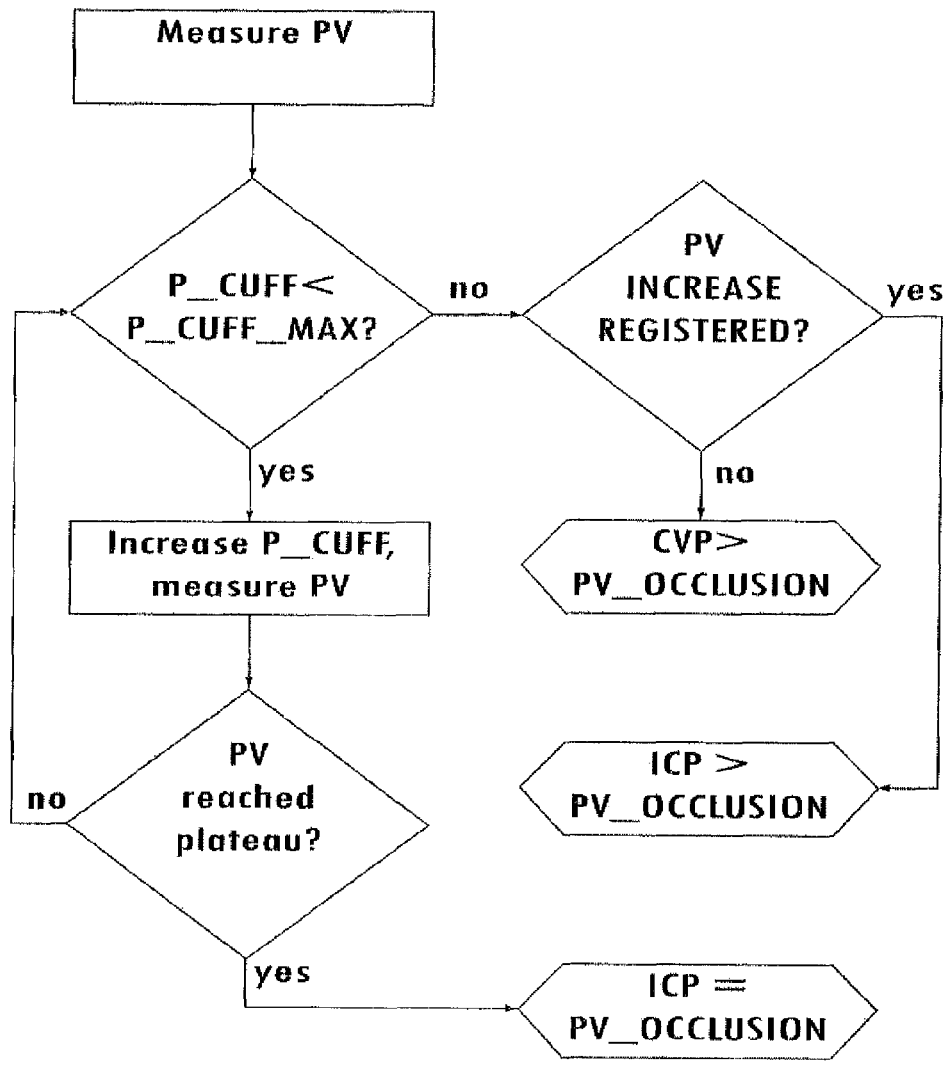
FIG. 4 is a schematic flow diagram depicting program flow in one embodiment of the inventive method.

FIG. 4 depicts an algorithm for detecting ICP using the cuff 30 and cuff controller 34 in FIG. 3, without cerebral NIRS device 40 and sensors 42. Accuracy of the detected pressure at which redistribution to VVP is improved, however, using the cerebral NIRS device 40/sensors 42. In more detail, when a measured P_Cuff causes collapse at 22 in the JV, a change in flow and cerebral blood volume noted by NIRS sensor 42 indicates equilibration of jugular pressure with ICP. Otherwise, if jugular veins would be in the collapsed state before cuff inflation, CBF would be redirected through VVP and no noticeable intracranial change in pressure (PV) would occur with cuff inflation. That is, to measure PV with JV occlusion, pressure, and/or blood volume in the head or cervical vein is measured and cervical cuff 30 is gradually inflated.

Vein pressure PV may be said to reach a "plateau" when further cuff inflation does not increase venous pressure. This state (or plateau) is displayed as PV_OCCLUSION, for example, in display device 52. FIG. 5A shows this plateau to be approximately $18^+$ mm HG, where FIG. 5 and FIG. 5B shows the plateau at around $20^-$ mm HG. Cuff inflation is limited to a maximum safe cuff pressure P_CUFF_MAX, which is selected below diastolic arterial pressure and inspiratory airway occlusion pressure. P_CUFF_MAX may be selected as 20 mm Hg (ICP treatment threshold) or higher. If initial PV is high and does not increase with extrinsic compression, effective cerebral outflow pressure is said to be determined by CVP, not the ICP. If PV increases with P_CUFF inflation, but does not reach the plateau at P_CUFF_MAX, the effective outflow pressure or ICP is displayed as higher than P_CUFF_MAX. FIG. 5C shows a condition in which a plateau is not reached regardless of increasing cuff pressure, so no redistribution occurs.

Venous pressure also may be changed with tonometric compression device, i.e., using a tonometric sensor over, jugular vein with complete or partial contralateral vein occlusion, or using a Valsalva maneuver/PEEP, intravascular catheter or by changing body position, such as reverse Trendelenburg position or head tilt (see FIG. 6). Effect on blood volume can be assessed with plethysmogram or time of flight measurement, and venous flow can be assessed along the spinal canal as well. For that matter, and in addition to the use of cerebral NIRS, Q_VVP and Q_JV may be assessed directly with ultrasound and their ratio is determined at different degrees of cervical compression or head elevation, where degree of cervical compression at which cerebral outflow is nearly equally distributed between VVP and jugular veins JV corresponds to effective outflow pressure or ICP.

FIG. 6 depicts another embodiment of a system for detecting and measuring increased global or local intracranial pressure. The system depicted in FIG. 6 causes outflow redistribution through the use of a head up-tilt using a tilt table 60 and an oscillometric device 70. Oscillometric device (oscillator/gyro accelerometer) 70, under control of processor 50 or some other means for controlling same (not shown in the figure), applies a series of short pressure signals about the neck sufficient to partially constrict the jugular veins, periodically. These external pressure signals are transmitted through the blood (including intracranially). An amplitude of these period signals is detectable, but limited and otherwise affected by ICP (see below).

The tilt table 60 preferably includes a gyroscope and is controlled by table controller 62. Both tilt table 60 and tilt table controller 62 are shown electrically connected to processor 40. For that matter, the tilt table may be controlled by the processor. In this tilt table arrangement, extrinsic cervical pressure stays the same. (atmospheric), while intraluminal pressure is lowered with head-up tilt by hydrostatic column of the height H (mm Hg). Jugular flow Q_JV or volume is estimated with H=0. Further head elevation causes jugular compression 22 and outflow redistribution to VVP. Head elevation to height H causes significant portions of jugular flow to be diverted to VVP (Q_VVPwQ_JV). This state corresponds to effective outflow pressure or ICP: hydrostatic column height H in mmHg equals ICP.

In operation, as the tilt-table is tilted, measurement and verification of pressure (in mm of Hg) at redistribution (from the JV to the VVP), is identified by cooperation of induced oscillations generated by an oscillometric device 70 at the jugulars and detection of the effect of same in the intracranial flow by an near infrared spectroscopy (NIRS) sensor 42 attached to the cranium 10, as shown. That is, an amplitude of an induced oscillation (by oscillator/gyro accelerometer 70) in the blood fluid is detected/measured by near infrared sensor (NIRS) 42. While only one NIRS sensor 42 is shown, two sensors 42 attached to locations corresponding to the left and right hemispheres may be used to identify differences in respective differences in blood volume or flow, affected by ICP. In cooperation with processing by processor 50, ICP values corresponding to the left and right hemispheres are displayed. Tilt angle may be detected using a gyroscope or accelerometer embedded with the tilt table 60, the tiltable controller 62 or the oscillometric device 70.

Effect on blood volume can be assessed with plethysmogram or time of flight measurement, and venous flow can be assessed along the spinal canal as well. Jugular outflow Q_JV is calculated as mean jugular linear flow times the jugular crossection area. Relative reduction of the jugular flow with cervical compression or head-up tilt reflects outflow diversion towards VVP. The height of head elevation or the degree of neck compression at the point when cerebral outflow is diverted towards VVP corresponds to the effective outflow pressure or ICP.

FIG. 7 is a schematic diagram depicting a variation on the FIG. 3 system for detecting and measuring increased global or local intracranial pressure about a patient facing out to highlight the feature by which the cerebral NIRS system 40 is able to localize ICP in the right and left hemisphere (using right and left sensors 42). Intracranial blood outflow designating arrows are shown in the two exiting jugular veins (IJ) on either side of the venous vertebral plexus VVP). As should be clear from FIG. 7, the outflow diversion (i.e., redistribution) from jugular veins (JV) to the vertebral venous plexus (VVP) with cervical cuff compression is measured and verified by the pair of NIRS sensor(s) 42 arranged on the patient's head. The pressure is calculated by the signals generated by each sensor, enabling localization of ICP in the right and left hemispheres. Of course the inventive operation may be enhanced by use of induced oscillations (See FIGS. 6, 9 and 13).

FIG. 8 is a schematic diagram depicting outflow diversion from jugular veins (JV) to vertebral venous plexus (VVP) with head elevation controlled by use of a calibrated tilt table 60 in combination with cuff occlusion (using cuff controller 34 and cuff 30 interconnected by conduit 36). The FIG. 8 system uses the cuff with gradual increase in mean pressure through use of tilting to better effect redistribution, if possible in view of ICP. While not shown in FIG. 8, induced oscillation (as depicted in the FIG. 7 system) is optional. If oscillation is used, maximal oscillation signal transmission (through the intracranial veins to the points proximate NIRS sensors 42) occurs when cuff pressure equals venous pressure (PV). If oscillation is not used, venous occlusion pressure can be detected as minimal cuff pressure at which cerebral blood volume reaches plateau during inflation or starts to decrease during deflation (indicating redistribution). That is, the head is elevated and the neck is compressed concurrently to simulate predetermined effective cerebral outflow pressure value (corresponding to treatment or diagnostic threshold, e.g., 20 mm Hg). If this does not result in significant cerebral outflow diversion, ICP is then estimated to be above said threshold value.

FIG. 9 is a schematic diagram depicting another embodiment of a system for detecting and measuring increased global or local intracranial pressure, The FIG. 9 system includes the use of cuff controller 34 with cuff 30, oscillator/gyro accelerometer 70 and cerebral near infrared spectroscopy (NIRS) device 40 with (NIRS) sensor(s) 42, all under control of processor 50. In the patient's cranium 10, outflow diversion from jugular veins (JV) to the vertebral venous plexus (VVP) occurs where cervical cuff 30 compression (pressure) sufficiently occludes JV venous outflow such that induced oscillation by centrally located oscillator 70 are no longer detected by an NIRS sensor 42, distal from cuff. That is, to determine ICP, jugular veins (JV) are occluded 22 with the inflatable cervical cuff 30 and equilibrium pressure (PV) is measured in the head or cervical vein (see FIG. 4). Once pressure in the cuff $P_C$ becomes equal to the pressure in the jugular vein, $P_{JV}$, transmission of the external oscillation to the jugular vein by oscillator 70 at cuff 30 is maximal and can be registered with the NIRS sensor 42 on the subject patient's head. This occlusion pressure (PV) represents effective outflow pressure (ICP if ICP is higher than CVP).

Put another way, the FIG. 9 setup or system uses mechanical oscillatory device located proximally to the cuff. Once cuff occludes jugular vein, transmission of oscillatory signal to the head ceases (no longer detected by the sensors 42). The minimal cuff pressure required to stop oscillatory signal transmission to the head is equated with ICP. The oscillometric device is attached to the neck or chest with adhesive. Oscillation is introduced, for example, by an eccentric vibratory motor. Oscillation amplitude is measured by the accelerometer and head tilting is measured by the gyroscope. Ratio of registered NIRS signal oscillation to the oscillator oscillation amplitude registered by the accelerometer determines oscillation transmission. When jugular vein reaches collapsed state indicating equilibration with the ICP, this ratio approaches zero.

FIG. 10 is a schematic diagram depicting another embodiment of a system for detecting and measuring increased global or local intracranial pressure. In FIG. 10, outflow diversion from jugular veins (JV) to the vertebral venous plexus (VVP) is implemented using an occlusion balloon 88 connected to a pressure sensor 85. The fluid volume of occlusion balloon is controlled by a pump 87, as shown. Pressure sensor 85 generates a pressure signal and communicates the signal to processor 50, with display 52. Sensor 85 with balloon 88 may be said to cooperate as an invasive jugular venous occlusion pressure measuring device, which uses balloon catheter occlusion of the jugular vein Once balloon occludes jugular vein, pressure in the jugular vein distally to occlusion balloon is jugular occlusion pressure, which approximates ICP. The pressure required to effect occlusion and, therefore, redistribution from JV to VVP is approximately equivalent to ICP.

Effect on venous flow can be assessed via Doppler, B-mode scan, color Doppler. In yet another embodiment, cerebral blood flow CBF is estimated with transcranial Doppler ultrasound measuring middle cerebral artery (MCA) blood flow linear velocity.

FIG. 11 is a schematic diagram depicting another embodiment of a system for detecting and measuring increased global or local intracranial pressure. The FIG. 11 system includes a liquid occlusion cuff 95 connected to a pressure sensor 92. Liquid occlusion cuff 95 provides occlusion pressure to the neck and jugular veins (JV), which is measured by sensor, Jugular collapse (indicating occlusion-induced diversion of venous outflow to VVP) is observed by use of an ultrasound probe 100. That is, device 100 is an ultrasound probe using two dimensional (duplex), motion (Doppler) or unidirectional (M) scanning modes. Outputs from ultrasound probe 100 and pressure senor 92 are processed by processor 52. Processing results are displayed using display device 52 (or transmitted to any other device for communicating the results known to the skilled artisan, for example, audio alarms, flashing lights, etc, depending on the detected ICP.

FIG. 12 is a schematic flow diagram depicting program flow in another embodiment of the inventive method for detecting and measuring increased global or local intracranial pressure. In a step 110, the method includes performing controlled occlusion of jugular cranial blood outflow. In a method step 120, the method includes generating occlusion data related to said controlled occlusion and in a method step 130, the method includes processing jugular cranial blood outflow occlusion data and blood outflow data relating to the controlled occlusion to identify and/or measure a functional relationship between the jugular controlled occlusion and the jugular cranial blood outflow.

NIRS sensor detects volume. dV/dt divided by dP/dt gives compliance. Where dP/dt is heart pulse (arterial or venous), respiratory pulse or external oscillation with amplitude measured by the accelerometer. The signal generated is normalised using DC component which exponentially decays with the length of the pathway. Maybe ad that to determine compliance/transmural pressure of extra- and intra-cranial blood vessels, transmural pressure can be affected by the head tilting, jugular occlusion, changing intra thoracic pressure and registering spontaneous variations in the arterial and venous blood pressure The method depicted in FIG. 12 can also include more or fewer number of steps. Further, the order of the steps may also vary.

For that matter, the above-described methods according to the present invention can be realized in hardware or as software or computer code that can be stored in a recording medium such as a CD ROM, an RAM, a floppy disk, a hard disk, or a magneto-optical disk or downloaded over a network, so that the methods described herein can be executed by such software using a general purpose computer, or a special processor or in programmable or dedicated hardware, such as an ASIC or FPGA. As would be understood in the art, the computer, the processor or the programmable hardware include memory components, e.g., RAM, ROM, Flash, etc. that may store or receive software or computer code that when accessed and executed by the computer, processor or hardware implement the processing methods described herein.

FIG. 13 is a schematic diagram depicting another embodiment of a system for detecting and measuring increased global or local intracranial pressure. In the FIG. 13 system, one or more NIRS sensors 42 is/are attached to the head with inflatable compression cuff 53, shown with dashed lines in the figure. Pressure is generated in the inflatable pressure cuff 53 by bladder and cuff controller 38, which also controls pressure in cervical cuff 30. For that matter, bladder and cuff controller 38 as shown is able to generate pulsed pressure signals to generate oscillatory signals in the blood fluid, as described with respect to oscillator 70 shown in FIGS. 6 and 9. Alternatively, an oscillator may be used in the FIG. 13 embodiment. Once pressure in the extracranial tissues (indicated as ECBF) equilibrates to the intracranial tissues (indicated as CBF), blood volume oscillation in the extracranial (ECBF) and intracranial (CBF) veins is approximately the same.

If NIRS sensor is pressed to the head with the pressure equal to the intracranial pressure, extracranial pressure equilibrates to intracranial pressure, thus oscillatory amplitude equilibrates: short-AC/DC approximates long-AC/DC. Or extracranial oscillation (short-AC/DC) approximates intracranial ([long-AC−short-AC]/[long-DC−short-DC]. Thus applying external pressure to the NIRS sensor, one can determine external pressure equilibration point with intracranial pressure. Adding external oscillation improves precision of this determination, as venous oscillation amplitude depends more on external pressure than arterial oscillation amplitude and because veins contain higher proportion (about 75%) of tissue blood volume.

Where there is an elevated ICP, however, the oscillatory signal detected in the extracranial blood flow (ECBF) will have an amplitude that is higher that the oscillatory signal detected in the intracranial blood flow (CBF), assuming transmural equilibration. For that matter, the magnitude of this detected difference in the left and right hemispheres provides for localized ICP values.

FIG. 14 presents a more detailed view of the compressive cranial cuff 47 and one of the NIRS sensors 42, as shown in FIG. 13. NIRS sensors have one light source or emitter and at least two light detectors (proximal, close, and distal, far). Transmitted light from the source passes into and returned from the extracranial and intracranial tissues. Tissue penetration depth by light is about half of the distance between emitter and detector. Short light pathway (light source to proximal, close, detector) is more superficial than the long pathway(source to distal, far; detector). To obtain signal preferably from the intracranial tissue these signals are commonly subtracted in today's near infrared devices.

Using the close detector of sensor 42, short (superficial or extracranial) trans illumination paths are observed, where using the far detector of sensor 42 long (deep or intracranial) trans illumination paths are observed. If NIRS sensor is applied to the head with pressure equal to intracranial, transmural pressure in the extracranial and intracranial compartments equilibrates. With equal transmural pressure compliance of the collapsible vessels equilibrates and volume oscillation amplitude whether intrinsic or externally induced equilibrates.

Volume pulsations in veins in general directly follow magnitude of the transmural pressure. Because pressure in the extracranial and intracranial compartments is different, oscillation of blood volume caused by pulsatile and respiratory variations or by extrinsic oscillation in these compartments is also different. These oscillations are commonly normalized to the tissue volume as AC/DC components of the signal. Thus we have two oscillations: short-AC/DC and long-AC/DC. Due to different transmural pressures in extracranial-intracranial vessels, compliances in the extracranial-intracranial compartments, are not equal. Using inherent oscillatory signals (arterial or venous), a difference between the signals detected in the extracranial blood flow (ECBF) and the intracranial blood flow (after transmural equilibration is affected by external cuff pressure at the detector 42), from which the elevated ICP is quantified.

In the foregoing description, certain terms and visual depictions are used to illustrate the preferred embodiment. However, no unnecessary limitations are to be construed by the terms used or illustrations depicted, beyond what is shown in the prior art, since the terms and illustrations are exemplary only, and are not meant to limit the scope of the present invention.

It is further known that other modifications may be made to the present invention, without departing the scope of the invention, as noted in the appended Claims.

What is claimed is:

1. A method for detecting and measuring increased global or local intracranial pressure within a subject cranium, comprising:

using noninvasive spectroscopy measuring means, creating and investigating a first light pathway through a portion of extracranial tissue, including blood pathways, surrounding the subject cranium and a second light pathway through a portion of intracranial tissue, including blood pathways, within the subject cranium, wherein the portion of extracranial tissue is proximate the portion of intracranial tissue;

applying a pressure at a measurable external pressure value to compel the noninvasive infrared spectroscopy measuring means against the subject cranium while detecting a first signal corresponding to a constant or average blood pressure (DC), and a second signal corresponding to a peak, pulsed blood pressure (AC) in both the extracranial and intracranial portions; and processing the measured external pressure value and the signals in the extracranial portion and the intracranial portion as the applied pressure is increased, until a state of compliance or equilibrium between the extracranial and intracranial blood vessels is detected, the measured pressure at which state corresponding to the subject cranium's intracranial pressure (ICP) proximate the noninvasive infrared spectroscopy measuring means.

2. The method as set forth in claim 1, wherein the processing includes processing both the first and second signals in the extracranial portion and the intracranial portion.

3. The method as set forth in claim 1, wherein in the step of applying, the first and second signals detect either blood flow or blood volume in the respective extracranial and intracranial regions.

4. The method as set forth in claim 1, wherein the noninvasive spectroscopy means comprises at least one NIRS sensor in electronic communication with an NIRS spectroscopy device and attached to the subject cranium capable of generating and investigating light path through both the extracranial portion and the intracranial portion.

5. The method as set forth in claim 1, wherein the pulsatile nature reflected in the pulsed blood pressure (AC) is driven by the subject's heart or breathing.

6. The method as set forth in claim 1, wherein the pulsatile nature reflected in the pulsed blood pressure (AC) is driven by oscillatory device.

7. The method as set forth in claim 6, wherein the oscillatory device is positioned at or near the subject's neck to effect the arterial blood vessels delivering blood to the extracranial and the intracranial blood pathways.

* * * * *